(12) United States Patent
Moon et al.

(10) Patent No.: US 8,263,769 B2
(45) Date of Patent: Sep. 11, 2012

(54) PROCESS FOR PREPARING VORICONAZOLE

(75) Inventors: Young Ho Moon, Suwon-si (KR); Moon Sub Lee, Bucheon-si (KR); Jae Ho Yoo, Osan-si (KR); Ji Sook Kim, Gyeonggi-do (KR); Han Kyong Kim, Yongin-si (KR); Chang Ju Choi, Seoul (KR); Young Kil Chang, Seoul (KR); Gwan Sun Lee, Seoul (KR)

(73) Assignee: Hanmi Science, Hwaseong-si (KR)

( * ) Notice: Subject to any disclaimer, the term of this patent is extended or adjusted under 35 U.S.C. 154(b) by 276 days.

(21) Appl. No.: 12/669,002

(22) PCT Filed: Aug. 4, 2008

(86) PCT No.: PCT/KR2008/004516
§ 371 (c)(1),
(2), (4) Date: Jan. 13, 2010

(87) PCT Pub. No.: WO2009/020323
PCT Pub. Date: Feb. 12, 2009

(65) Prior Publication Data
US 2010/0190983 A1    Jul. 29, 2010

(30) Foreign Application Priority Data
Aug. 6, 2007    (KR) ........................ 10-2007-0078439

(51) Int. Cl.
*C07D 403/06* (2006.01)
*C07D 239/38* (2006.01)
(52) U.S. Cl. ...................................... 544/319; 544/333
(58) Field of Classification Search .................. 544/319, 544/333
See application file for complete search history.

(56) References Cited

U.S. PATENT DOCUMENTS 6,586,594 B1    7/2003    Butters et al.

FOREIGN PATENT DOCUMENTS

| | | |
|---|---|---|
| CN | 1488630 A | 4/2004 |
| CN | 1814597 A | 8/2006 |
| EP | 0440372 A1 | 8/1991 |
| GB | 2452049 A | 2/2009 |
| WO | 93/07139 A1 | 4/1993 |
| WO | 97/06160 A1 | 2/1997 |
| WO | 2006/065726 A2 | 6/2006 |
| WO | 2007/013096 A1 | 2/2007 |
| WO | 2007/132354 A2 | 11/2007 |
| WO | WO 2009/024214 * | 2/2009 |
| WO | 2009/084029 A2 | 7/2009 |

OTHER PUBLICATIONS

European Patent Office, EP Search Report issued in corresponding EP Application No. 08793030.1, dated Feb. 22, 2011.
Butters et al., "Process Development of Voriconazole: A Novel Broad-Spectrum Triazole Antifungal Agent," Organic Process Research & Development, 2001, vol. 5, pp. 28-36.

\* cited by examiner

*Primary Examiner* — Deepak Rao
(74) *Attorney, Agent, or Firm* — Sughrue Mion, PLLC

(57) ABSTRACT

Optically pure voriconazole can be prepared in a high yield by a) subjecting 1-(2,4-difluorophenyl)-2(1H-1,2,4-triazol-1-yl)ethanone to Reformatsky-type coupling reaction with a substituted thiopyrimidine derivative to obtain a desired (2R, 3S)/(2S,3R)-enantiomeric pair; b) removing the thiol derivative from the enantiomer to obtain racemic voriconazole; and c) isolating the racemic voriconazole by way of optical resolution using an optically active acid.

7 Claims, No Drawings

PROCESS FOR PREPARING VORICONAZOLE

This application is a 371 of PCT/KR08/04516 filed Aug. 4, 2008, which claims priority from Korean Patent Application No. 10-2007-0078439 filed Aug. 6, 2007.

FIELD OF THE INVENTION

The present invention relates to a novel process for preparing voriconazole.

BACKGROUND OF THE INVENTION

Voriconazole, (2R,3S)-2-(2,4-difluorophenyl)-3-(5-fluoropyrimidin-4-yl)-1-(1H-1,2,4-triazol-1-yl)butan-2-ol having the structure of formula (I), is an antifungal drug used for preventing or treating fungal infection, e.g., human local fungal infection caused by *candida, trichophyton, microspourum* or *epidemophyton*; mucosal infection, by *candida albicans* (e.g., thrush and candidiasis); and whole body fungal infection, by *aspergilus*.

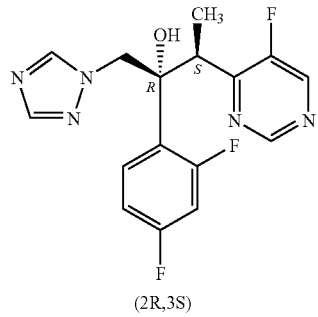

(2R,3S)

Voriconazole has two asymetric carbon atoms, and therefore, 4 stereoisomers, enantiomers of two diastereomeric pairs are involved in the preparation thereof which is generally conducted by a) separating an enantiomeric pair having (2R,3S) and (2S,3R) configurations; and then b) separating the (2R,3S)-stereoisomer using an optically active acid (e.g., R-(−)-10-camphosulfonic acid). The structural specificity and instability under a basic condition make the stereoselective synthesis of voriconazole difficult.

To date, only two methods for preparing voriconazole have been reported. One is based on a coupling reaction using an organic lithium salt, and the other, on Reformatsky-type coupling reaction.

For example, Korean Patent No. 1993-0011039 and European Patent No. 0,440,372 disclose a method shown in Reaction Scheme A for preparing the desired enantiomeric pair by a) adding an organic lithium derivative of 4-chloro-6-ethyl-5-fluoropyrimidine to 1-(2,4-difluorophenyl)-2-(1H-1,2,4-triazol-1-yl)ethanone at −70° C.~−50° C. to obtain an enantiomer mixture; and b) separating the desired enantiomer by chromatography.

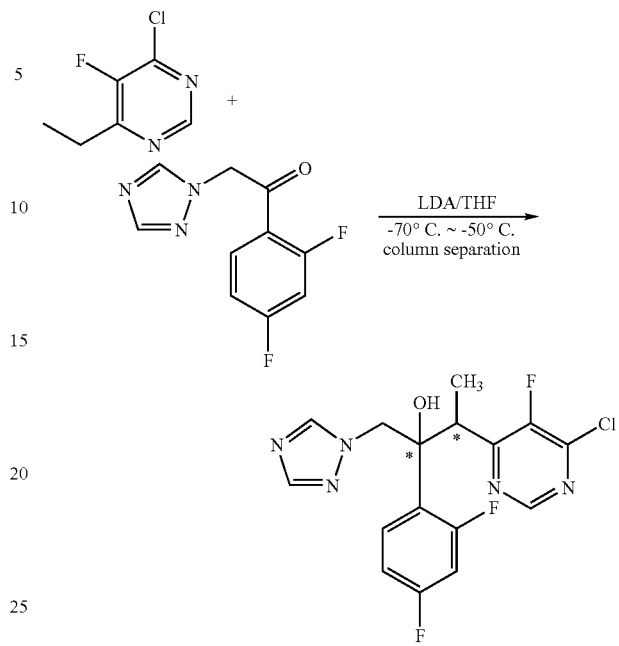

However, this coupling reaction using a strong base such as LDA or NaHMDS produces (2R,3S)/(2S,3R) and (2R,3R)/(2S,3S) diastereomers in a mole ratio of 1.1:1 without stereoselectivity, and the desired (2R,3S)/(2S,3R)-enantiomeric pair is isolated in a yield of only 12~25%. Further, the lithium salt used in the reaction is difficult to be applied to mass production because of the required anhydrous condition at −78° C.

PCT Publication No. WO 2006/065726 discloses a method shown in Reaction Scheme B for preparing the desired enantiomeric pair by repeating the procedure of Reaction Scheme A except for using a different solvent.

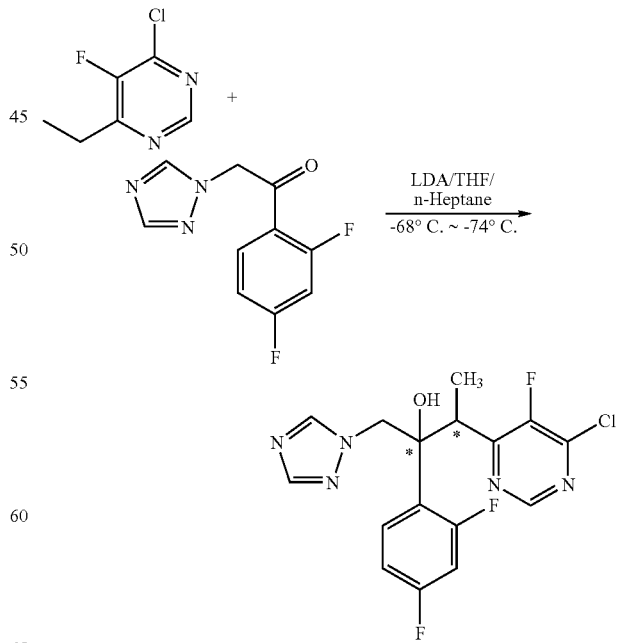

However, despite the merit of this reaction which allows the separation of the desired enantiomeric pair by crystallization, it is hampered by the same problems associated with Reaction Scheme A and the yield of the desired enantiomeric pair is only 26%.

In order to solve the problems, as shown in Reaction Scheme C, Korean Patent Publication No. 1999-0036174 and U.S. Pat. No. 6,586,594 B1 disclose a method for preparing voriconazole by conducting Reformatsky-type reaction to enhance the stereoselectivity and yield, and then reductively removing the chlorine substituent in the presence of a palladium catalyst.

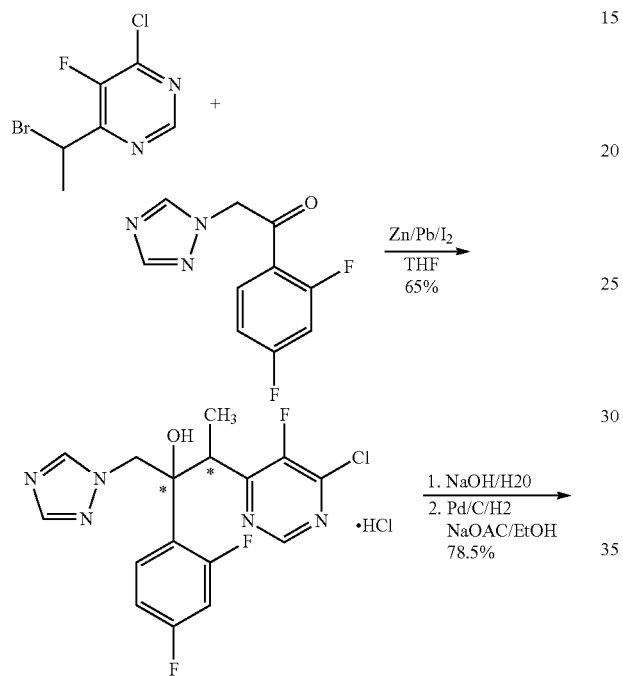

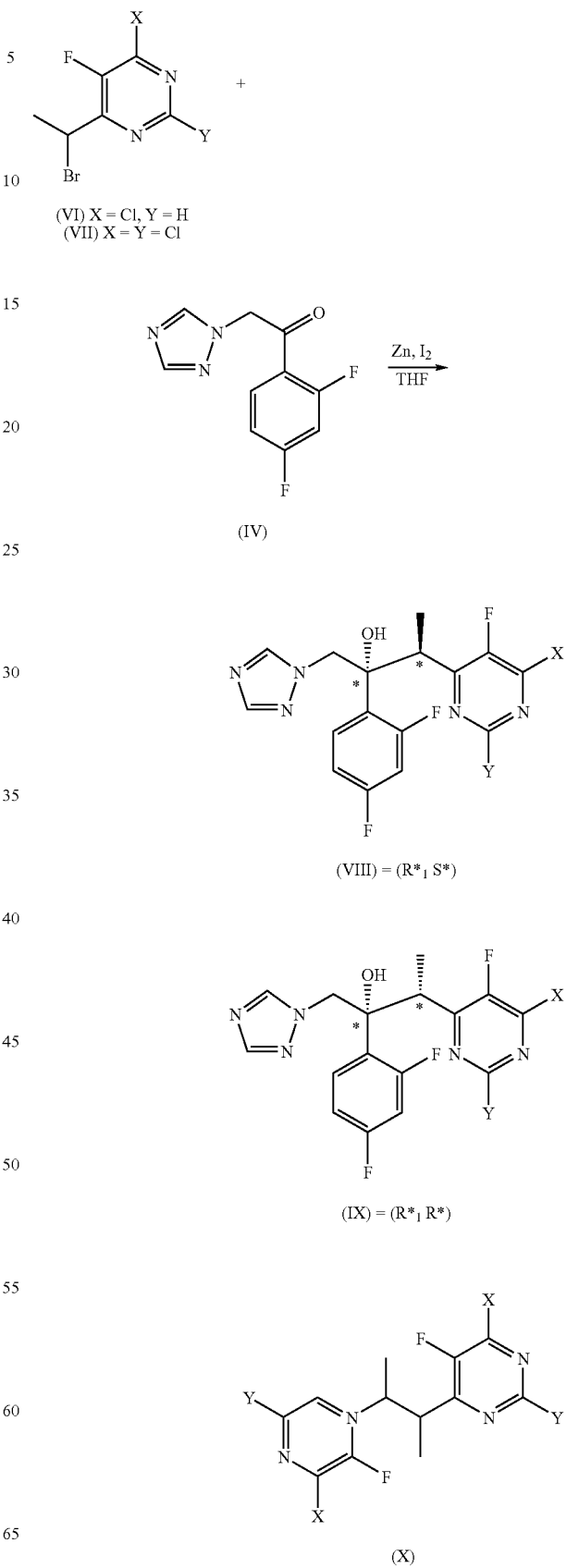

In this reaction, the (2R,3S)/(2S,3R)- and (2R,3R)/(2S,3S)-enantiomeric pairs were formed in a mole ratio of 9:1, and the yield of the isolated voriconazole hydrochloride was as high as 65%. However, the pyrimidine derivative used as a starting material is difficult to remove when remains unreacted, which leads to the lowering of the product purity.

Further, the literature ([Organic Process Research & Development 2001, 5, 28-36], Pfizer Inc.) teaches that the chlorine substituent of the pyrimidine derivative adversely influences the coupling reaction pattern as shown in Reaction Scheme D and Table 1.

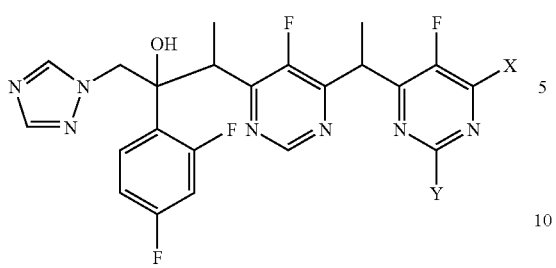

(XI)

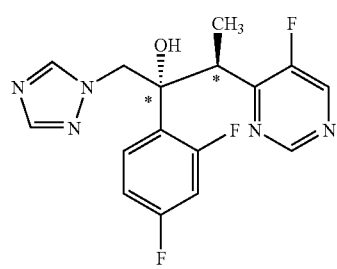

(2R, 3S/2S, 3R)

TABLE 1

Reformatsky-type reaction of compounds (VI, VII) and (IV)

| Pyrimidine | Compound (VIII) (%) | Compound (IX) (%) | Unreacted pyrimidine (%) | Debrominated pyrimidine (%) | Compound (X) (%) | Compound (XI) (%) |
|---|---|---|---|---|---|---|
| Compound (VI) | 47.5 | 24.0 | 0.0 | 15 | 4.3 | 9.2 |
| Compound (VII) | 5.3 | 4.6 | 8.5 | 28 | 0.0 | 51.6 |

Example 1 of Korean Patent Publication No. 1999-0036174 (see Reaction Scheme C) shows that the (2R,3S)/(2S,3R)- and (2R,3R)/(2S,3S)-enantiomeric pairs were obtained in a mole ratio of 10:1, but the product mixture contained unreacted compound of formula (IV) (7%) and unknown byproduct suspected to be the compound of formula (XI) (14%). Thus, the procedure of Reaction Scheme C gives an impure product mixture, the isolation of the desired product by recrystallization giving only a yield of 40~45%.

SUMMARY OF THE INVENTION

Accordingly, it is an object of the present invention to provide an improved process for preparing optically pure voriconazole in a high yield.

In accordance with one aspect of the present invention, there is provided a process preparing voriconazole of formula (I) comprising the steps of:

a) subjecting the compound of formula (IV) to Reformatsky-type coupling reaction with a compound of formula (V) to obtain a compound of formula (III) which is a (2R,3S)/(2S,3R)-enantiomeric pair;

b) removing the thiol derivative from the compound of formula (III) to obtain the racemic voriconazole of formula (II); and c) isolating the compound of formula (II) by way of optical resolution using an optically active acid.

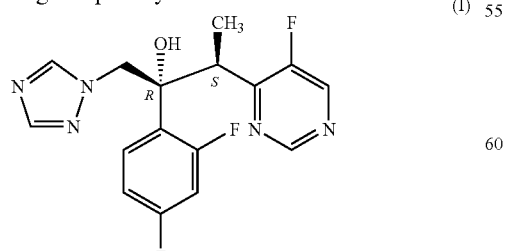

(2R, 3S)

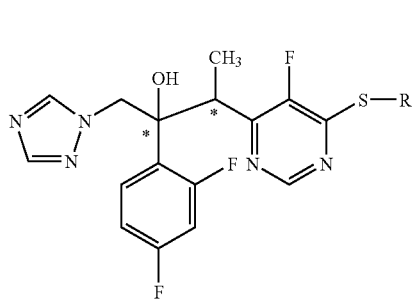

(2R, 3S/2S, 3R)

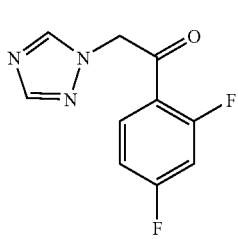

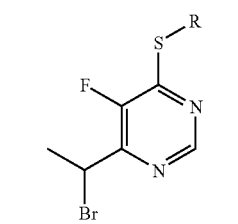

wherein,

R is $C_1$-$C_4$ alkyl, benzothiazolyl, benzoxazolyl, imidazolyl, 1-methylimidazolyl, thiazolyl, pyridyl, pyrimidyl, phenyl, or phenyl having one or two substituents selected from the group consisting of halogen, nitro and methoxy.

DETAILED DESCRIPTION OF THE INVENTION

According to the present invention, voriconazole may be prepared by the procedure shown in Reaction Scheme E.

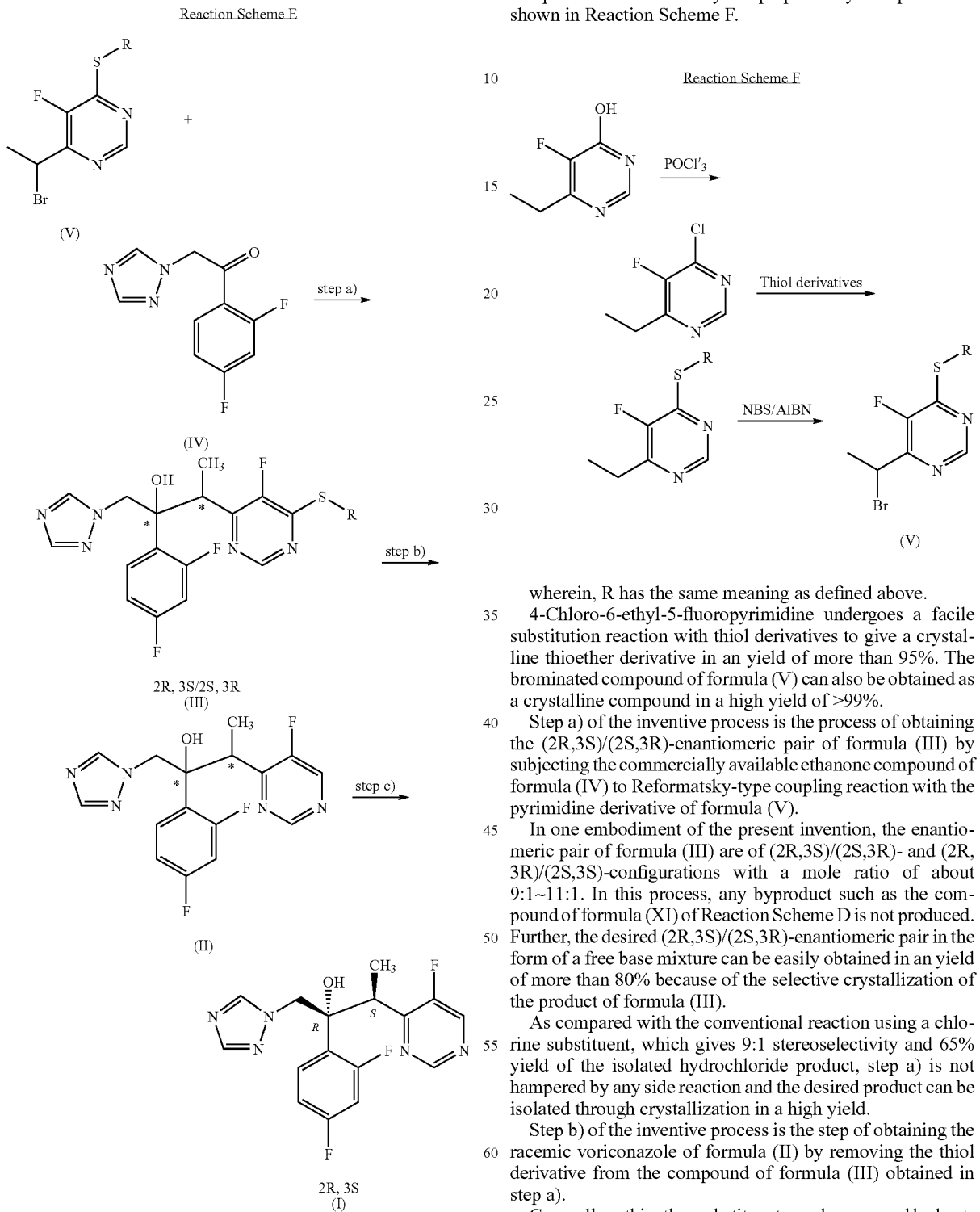

wherein,
R has the same meaning as defined above. Preferably, R is phenyl or 4-chlorophenyl.

The compounds of formulae (V) and (III) used in Reaction Scheme E are each a crystallizable, stable and novel compound. The procedure shown in Reaction Scheme E is explained below in details.

The compound of formula (V) used as a starting material of the present invention may be prepared by the procedure shown in Reaction Scheme F.

wherein, R has the same meaning as defined above.

4-Chloro-6-ethyl-5-fluoropyrimidine undergoes a facile substitution reaction with thiol derivatives to give a crystalline thioether derivative in an yield of more than 95%. The brominated compound of formula (V) can also be obtained as a crystalline compound in a high yield of >99%.

Step a) of the inventive process is the process of obtaining the (2R,3S)/(2S,3R)-enantiomeric pair of formula (III) by subjecting the commercially available ethanone compound of formula (IV) to Reformatsky-type coupling reaction with the pyrimidine derivative of formula (V).

In one embodiment of the present invention, the enantiomeric pair of formula (III) are of (2R,3S)/(2S,3R)- and (2R,3R)/(2S,3S)-configurations with a mole ratio of about 9:1~11:1. In this process, any byproduct such as the compound of formula (XI) of Reaction Scheme D is not produced. Further, the desired (2R,3S)/(2S,3R)-enantiomeric pair in the form of a free base mixture can be easily obtained in an yield of more than 80% because of the selective crystallization of the product of formula (III).

As compared with the conventional reaction using a chlorine substituent, which gives 9:1 stereoselectivity and 65% yield of the isolated hydrochloride product, step a) is not hampered by any side reaction and the desired product can be isolated through crystallization in a high yield.

Step b) of the inventive process is the step of obtaining the racemic voriconazole of formula (II) by removing the thiol derivative from the compound of formula (III) obtained in step a).

Generally, a thioether substituent may be removed by heating in the presence of a Raney Nickel catalyst (Tetrahedron 55, 523~95252 (1973)). However, when this method is applied to step b) of the inventive process, the reaction proceeds sluggishly, and the yield of the desired compound of formula (II) becomes only 30%~40%, besides the problem that the use of Raney Nickel is not suitable for mass production because of its flammability.

According to the present invention, zinc which is cheap and applicable to mass production and ammonium formate as a hydrogen donor are used in this step. In an embodiment, when zinc/ammonium formate together with water and organic solvent are used, the racemic voriconazole of formula (II) is obtained in a yield of more than 90% with 98.5% purity. Therefore, this process is more economic and effective than the reductive elimination of the thiol derivative using an expensive palladium metal catalyst, which is conventionally used to remove a chlorine substituent.

The zinc used in this reaction may be a commercially available zinc powder or an activated zinc prepared by treating the commercial zinc powder with 1N—HCl. The amount of the zinc used in this step is about 3 to 10 equivalents, preferably about 5 equivalents, based on the compound of formula (III).

The organic solvent used in this reaction may be at least one selected from the group consisting of an alcohol such as methanol, ethanol, and isopropanol; an ether such as tetrahydrofuran and dioxane; a ketone such as acetone and methylisobutylketone; a nitrile such as acetonitrile; and an amide such as dimethylacetamide and dimethylformamide, which can be used as a mixture with water, preferably, a mixture of tetrahydrofuran and water. The volume ratio of the solvent and water may be about 1:1 to 5:1, preferably about 3:2.

The reaction may be carried out at about 50° C. to 70° C., and the ammonium formate as a hydrogen donor may be added to the reacting solution in the form of an aqueous solution.

The above reaction is advantageous in that: the compound of formula (II) is obtained in a high purity (>98.5%) and yield (90%); and the cost of mass producing the desired compound using a cheap zinc is far cheaper as compared with the reductive elimination of the thiol derivative using expensive palladium or flammable Raney Nickel.

Step c) of the inventive process is the process of optically resolving the compound of formula (II) obtained in step b) using an optically active acid. The method of optically resolving a compound using an optically active acid is known in the art, and voriconazole of formula (I) can be isolated by any of the known optical resolution methods. Examples of the optically active acid used in this step include, without limitation, an acid addition salt such as R-(−)-10-camphosulfonic acid, and others.

The following Examples are intended to illustrate the present invention without limiting its scope.

Preparation Example 1

Preparation of 4-(1-bromo-ethyl)-6-(4-chloro-phenylsulfanyl)-5-fluoropyrimidine

<1-1> Preparation of 4-chloro-6-ethyl-5-fluoropyrimidine 78.24 ml of triethylamine was added to a solution prepared by dissolving 80 g of 6-ethyl-5-fluoro-4-hydroxypyrimidine in 240 ml of dichloromethane, and 57.4 ml of phosphorus oxychloride was slowly added thereto over 30 min. The resulting solution was refluxed for 5 hours to complete the reaction, and cooled to room temperature. Then, 352 ml of 3N HCl was added thereto while maintaining the temperature at below 20° C. The resulting aqueous mixture was extracted with 100 ml of dichloromethane. The organic layer was washed with 100 ml of water, was dried over magnesium sulfate, and concentrated under a reduced pressure to obtain the title compound as an oil (85.9 g, yield: 95%).

$^1$H-NMR (300 MHz, CDCl$_3$) δ (ppm): 8.70 (1H), 2.90 (2H), 1.34 (3H)

<1-2> Preparation of 4-(4-chloro-phenylsulfanyl)-6-ethyl-5-fluoropyrimidine 61.0 g of 4-chloro-6-ethyl-5-fluoropyrimidine was added to 600 ml of acetonitrile, and 60.4 g of 4-chlorothiophenol was added thereto followed by lowering the temperature to 10° C. 66.1 ml of diisopropylethylamine was added to the resulting solution, and reacted for 2 hours while maintaining the temperature at room temperature. 100 ml of dichloromethane and 300 ml of water were added to the resulting mixture to separate layer, and the resulting aqueous mixture was extracted with 300 ml of dichloromethane. The organic layer was dried over magnesium sulfate, concentrated under a reduced pressure, and crystallized at 5° C. in 305 ml of isopropanol and 122 ml of water to obtain the white title compound (85.6 g). Then, the filtrate was additionally concentrated under a reduced pressure, and crystallized at 5° C. in 30 ml of isopropanol to obtain 12.3 g of the title compound (total: 97.9 g, total yield: 96%).

m.p=44.1° C.~45.5° C.
$^1$H-NMR (300 MHz, CDCl$_3$) δ (ppm): 8.61 (1H), 7.47 (4H), 5.34 (1H), 2.04 (3H)

<1-3> Preparation of 4-(1-bromo-ethyl)-6-(4-chloro-phenylsulfanyl)-5-fluoropyrimidine 131 g of 4-(4-chloro-phenylsulfanyl)-6-ethyl-5-fluoropyrimidine, 103.8 g of N-bromosuccinimide and 7.98 g of azobisisobutyronitrile were dissolved in 850 ml of dichloroethane. The resulting mixture was refluxed for 2 hours, cooled to room temperature, and washed successively with 800 ml of water, 50 g of sodium metabisulfite in 950 ml of water and 500 ml of brine. The resulting solution was concentrated under a reduced pressure and crystallized at 5° C. in 391 ml of isopropanol to obtain the white compound, and the compound was washed with 50 ml of isopropanol at 5° C. to obtain the white title compound (150.7 g, yield: 89%).

m.p=86.2° C.~87.5° C.
$^1$H-NMR (300 MHz, CDCl$_3$) δ (ppm): 8.61 (1H), 7.47 (4H), 5.34 (1H), 2.04 (3H)

Preparation Example 2

Preparation of 4-(1-bromo-ethyl)-6-(4-phenylsulfanyl)-5-fluoropyrimidine

<2-1> Preparation of 4-(phenylsulfanyl)-6-ethyl-5-fluoropyrimidine 40 g of 4-chloro-6-ethyl-5-fluoropyrimidine was added to 400 ml of acetonitrile, and 28 ml of thiophenol was added thereto, followed by lowering the temperature to 10° C. 43.39 ml of diisopropylethylamine was added to the resulting solution, and reacted for 2 hours while maintaining the temperature at room temperature. 65 ml of dichloromethane and 200 ml of water were added to the resulting mixture to separate layer, and the resulting aqueous mixture was extracted with 200 ml of dichloromethane. The organic layer was dried over magnesium sulfate and concentrated under a reduced pressure to obtain the title compound as an oil (63.6 g, yield: 95%).

¹H-NMR (300 MHz, CDCl₃) δ (ppm): 8.61 (1H), 7.59-7.42 (5H), 2.80 (2H), 1.30 (3H)

<2-2> Preparation of 4-(1-bromo-ethyl)-6-(4-phenyl-sulfanyl)-5-fluoropyrimidine 63.6 g of 4-(4-phenylsulfanyl)-6-ethyl-5-fluoropyrimidine, 72.8 g of N-bromosuccinimide and 5.77 g of azobisisobutyronitrile were dissolved in 500 ml of dichloroethane. The resulting mixture was refluxed for 2 hours, cooled to room temperature, and washed successively with 700 ml of water, 21 g of sodium metabisulfite in 480 ml of water and 380 ml of brine. The resulting solution was concentrated under a reduced pressure, crystallized at 5° C. in 391 ml of isopropanol, filtered and dried to obtain the white title compound (65 g, yield: 79%).

¹H-NMR (300 MHz, CDCl₃) δ (ppm): 8.62 (1H), 7.59-7.42 (5H), 5.36 (1H), 2.03 (3H)

Example 1

Preparation of (2R,3S)/(2S,3R)-3-[6-(4-chloro-phenylsulfanyl)-5-fluoro-pyrimidine-4-yl]-2-(2,4-difluoro-phenyl)-1-[1,2,4]triazol-1-yl-butane-2-ol 60 g of zinc powder treated with 1N HCl and 2.97 g of lead powder were added to 360 ml of tetrahydrofuran and stirred, and 45.04 g of iodine dissolved in 120 ml of tetrahydrofuran was slowly added thereto for 10 min. The resulting mixture was cooled to 5° C., and a solution dissolving 40 g of 1-(2,4-difluorophenyl)-2-(1H-1,2,4-triazol-1-yl)ethanone in 320 ml of tetrahydrofuran and 82.24 g of 4-(1-bromo-ethyl)-6-(4-chloro-phenylsulfanyl)-5-fluoropyrimidine obtained in Preparation Example 1 were slowly added thereto for 1 hr. The obtained mixture was heated to 25° C. and reacted for 1 hour.

Solid residue was filtered out and washed with 380 ml of ethyl acetate. 380 ml of a saturated ammonium chloride aqueous solution was added thereto, and the resulting aqueous mixture was removed therefrom. 1.2 ml of a saturated sodium bicarbonate aqueous solution was added to the organic layer and the pH was maintained at 7.6. The resulting aqueous mixture was washed with 100 ml of brine, dried over magnesium sulfate, and concentrated under a reduced pressure. The resulting concentrate was crystallized with 200 ml of isopropanol at 25° C., filtered and dried to obtain the pale yellow title compound as a form of free base (72 g, yield: 82%).

m.p=158.1° C.~159.6° C.

¹H-NMR (300 MHz, CDCl₃) δ (ppm): 8.52 (1H), 7.94 (1H), 7.62-7.45 (6H), 6.87-6.79 (2H), 6.53 (1H), 4.73 (1H), 4.19 (1H), 4.08 (1H), 1.09 (3H)

The ratio of the enantiomeric pair obtained from HPLC analysis of the reacting solution by using an internal standard material was 10:1, and the ratio of (2R,3S)/(2S,3R)- and (2R,3R)/(2S,3S)-enantiomeric pairs obtained from HPLC analysis of the crystallized solid was 99.8%:0.2%.

Example 2

Preparation of (2R,3S)/(2S,3R)-3-[6-(4-chloro-phenylsulfanyl)-5-fluoro-pyrimidine-4-yl]-2-(2,4-difluoro-phenyl)-1-[1,2,4]triazol-1-yl-butane-2-ol The procedure of Example 1 was repeated except for using 10 g of 1-(2,4-difluorophenyl)-2-(1H-1,2,4-triazol-1-yl)ethanone and 20.56 g of (1-bromo-ethyl)-6-(4-chloro-phenylsulfanyl)-5-fluoropyrimidine and not using the lead powder to obtain the pale yellow title compound (17.5 g, yield: 79%).

m.p=158.1° C.~159.6° C.

¹H-NMR (300 MHz, CDCl₃) δ (ppm): 8.52 (1H), 7.94 (1H), 7.62-7.45 (6H), 6.87-6.79 (2H), 6.53 (1H), 4.73 (1H), 4.19 (1H), 4.08 (1H), 1.09 (3H)

The ratio of the enantiomeric pair obtained from HPLC analysis of the reacting solution by using an internal standard material was 9.5:1, and the ratio of (2R,3S)/(2S,3R)- and (2R,3R)/(2S,3S)-enantiomeric pairs obtained from HPLC analysis of the crystallized solid was 99.8%:0.2%.

Example 3

Preparation of (2R,3S)/(2S,3R)-2-(2,4-difluorophenyl)-3-(5-fluoropyrimidin-4-yl)-1-(1H-1,2,4-triazol-1-yl)butane-2-ol 13.3 g of zinc powder treated with 1N HCl was dissolved in 300 ml of tetrahydrofuran and refluxed for 1 hour. The resulting solution was cooled to 50° C., and 20 g of (2R,3S)/(2S,3R)-3-[6-(4-chloro-phenylsulfanyl)-5-fluoro-pyrimidine-4-yl]-2-(2,4-difluoro-phenyl)-1-[1,2,4]triazol-1-yl-butane-2-ol obtained in Example 1 or 2 was added thereto. 7.71 g of ammonium formate dissolved in 200 ml of water was slowly added to the resulting mixture for 30 min, and refluxed for 4 hours. The reaction solution was cooled to room temperature, filtered and washed with 200 ml of ethyl acetate. The resulting residue was washed with 200 ml of saturated ammonium chloride aqueous solution, and the water layer was removed therefrom. The organic layer was washed with 200 ml of sodium bicarbonate and 200 ml of brine, and dried over magnesium sulfate. 200 ml of ethyl acetate and 100 ml of hexane were added to the resulting residue, and 9 ml of concentrated HCl was added thereto for crystallization. 200 ml of ethyl acetate and 200 ml of sodium bicarbonate were added to the obtained solid mixture and stirred for 10 min, and the resulting solid was filtered out by using celite. The resulting organic layer was washed with 200 ml of a 5% sodium hydroxide aqueous solution and concentrated under a reduced pressure to obtain the crystallized title compound (12.7 g, yield: 90%).

¹H-NMR (300 MHz, CDCl₃) δ (ppm): 8.93 (1H), 8.62 (1H), 7.97 (1H), 7.60 (1H), 7.54 (1H), 6.87-6.80 (2H), 6.48 (1H), 4.42 (1H), 4.32 (1H), 4.13 (1H), 1.11 (3H)

Example 4

Preparation of (2R,3S)/(2S,3R)-3-[6-(4-phenylsulfanyl)-5-fluoro-pyrimidine-4-yl]-2-(2,4-difluoro-phenyl)-1-[1,2,4]triazol-1-yl-butane-2-ol 19.42 g of zinc powder treated with 1N HCl and 0.96 g of lead powder were added to 162 ml of tetrahydrofuran and stirred, and 14.6 g of iodine dissolved in 51 ml of tetrahydrofuran was slowly added thereto for 10 min. The resulting mixture was cooled to 5° C., and a solution dissolving 12.96 g of 1-(2,4-difluorophenyl)-2-(1H-1,2,4-triazol-1-yl)ethanone in 135 ml of tetrahydrofuran, 24 g of 4-(1-bromo-ethyl)-6-(4-phenylsulfanyl)-5-fluoropyrimidine obtained in Preparation Example 2 and 1.18 g of iodine were slowly added thereto for 1 hr. The obtained mixture was heated to 25° C. and reacted for 2 hours.

Solid residue was filtered out and washed with 380 ml of ethyl acetate. 120 ml of a saturated ammonium chloride aqueous solution was added thereto, and the water layer was removed therefrom. 380 ml of a saturated sodium bicarbonate aqueous solution was added to the organic layer and the pH was maintained at 7.6. The resulting organic layer was washed with 120 ml of brine, dried over magnesium sulfate, and concentrated under a reduced pressure. The resulting concentrate was crystallized with 240 ml of isopropanol at 25° C., filtered and dried to obtain the pale yellow title compound (19.33 g, yield: 72.8%).

$^1$H-NMR (300 MHz, DMSO) δ (ppm): 8.86 (1H), 8.67 (1H), 7.62-7.45 (6H), 7.31 (2H), 6.93 (1H), 4.73 (1H), 4.43 (1H), 3.91 (1H), 1.08 (3H)

The ratio of the enantiomeric pair obtained from HPLC analysis of the reaction solution by using an internal standard material was 9:1, and the ratio of (2R,3S)/(2S,3R)- and (2R,3R)/(2S,3S)-enantiomeric pairs obtained from HPLC analysis of the crystallized solid was 99.9%:0.1%.

Example 5

Preparation of (2R,3S)/(2S,3R)-2-(2,4-difluorophenyl)-3-(5-fluoropyrimidin-4-yl)-1-(1H-1,2,4-triazol-1-yl)butane-2-ol 3.58 g of zinc powder treated with 1N HCl was dissolved in 75 ml of tetrahydrofuran and refluxed for 1 hour. The resulting solution was cooled to 50° C., and 5 g of (2R,3S)/(2S,3R)-3-[6-(4-phenylsulfanyl)-5-fluoro-pyrimidine-4-yl]-2-(2,4-difluoro-phenyl)-1-[1,2,4]triazol-1-yl-butane-2-ol obtained in Example 4 was added thereto. 2.07 g of ammonium formate dissolved in 50 ml of water was slowly added to the resulting mixture for 30 min, and refluxed for 4 hours. The reaction solution was cooled to room temperature, filtered and washed with 50 ml of ethyl acetate. The resulting residue was washed with 50 ml of a saturated ammonium chloride aqueous solution, and washed again with 50 ml of sodium bicarbonate and 50 ml of brine. The organic layer was dried over magnesium sulfate and concentrated under a reduced pressure. 50 ml of ethyl acetate and 25 ml of hexane were added to the resulting residue, and 2.2 ml of concentrated HCl was added thereto for crystallization. 50 ml of ethyl acetate and 50 ml of sodium bicarbonate were added to the obtained solid mixture and stirred for 10 min, and the resulting solid was filtered out by using celite. The filtrate was washed with 50 ml of 5% a sodium hydroxide aqueous solution and concentrated under a reduced pressure to obtain the crystallized title compound (3.9 g, yield: 81%).

$^1$H-NMR (300 MHz, CDCl$_3$) δ (ppm): 8.93 (1H), 8.62 (1H), 7.97 (1H), 7.60 (1H), 7.54 (1H), 6.87-6.80 (2H), 6.48 (1H), 4.42 (1H), 4.32 (1H), 4.13 (1H), 1.11 (3H)

Example 6

Preparation of (2R,3S)-2-(2,4-difluorophenyl)-3-(5-fluoropyrimidin-4-yl)-1-(1H-1,2,4-triazol-1-yl)butane-2-ol (R)-camsylate 10 g of (2R,3S)/(2S,3R)-2-(2,4-difluorophenyl)-3-(5-fluoropyrimidin-4-yl)-1-(1H-1,2,4-triazol-1-yl)butane-2-ol obtained in Example 3 or 5 was dissolved in 230 ml of acetone, and 6.64 g of R-(−)-10-camphosulfonic acid dissolved in 75 ml of methanol was added thereto. The resulting mixture was refluxed for 1 hour and slowly cooled to room temperature for crystallization while stirring overnight at 20° C. The resulting solution was filtered and dried to obtain the white title compound (6 g, yield: 36%).

The optical purity of the compound obtained from HPLC analysis was >99.9%.

Example 7

Preparation of (2R,3S)-2-(2,4-difluorophenyl)-3-(5-fluoropyrimidin-4-yl)-1-(1H-1,2,4-triazol-1-yl)butane-2-ol(voriconazole)

10 g of (2R,3S)-2-(2,4-difluorophenyl)-3-(5-fluoropyrimidin-4-yl)-1-(1H-1,2,4-triazol-1-yl)butane-2-ol (R)-camsylate obtained in Example 6 was added to a mixture of 50 ml of water and 50 ml of dichloromethane, and a 40% sodium hydroxide solution was slowly added thereto to adjust the pH to 11~12. The organic layer was separated therefrom and dried over magnesium sulfate, and the organic solvent was removed under a reduced pressure. The resulting solution was crystallized with 18 ml of isopropanol, cooled to 0° C., stirred for 2 hours, and dried to obtain the white title compound (5.56 g, yield: 93%).

m.p=134

$^1$H-NMR (300 MHz, DMSO-d$_6$) δ (ppm): 9.04 (1H), 8.84 (1H), 8.23 (1H), 7.61 (1H), 7.28 (1H), 7.17 (1H), 6.91 (1H), 5.97 (1H), 4.80 (1H), 4.34 (1H), 3.93 (1H), 1.1 (3H)

The optical purity of the compound obtained from HPLC analysis was >99.9%.

Comparative Example

Preparation of (2R,3S)/(2S,3R)-(2R,3R)/(2S,3S)-3-(4-chloro-5-fluoropyrimidine-6-yl)-2-(2,4-difluorophenyl)-1-(1H-1,2,4-triazol-1-yl)butane-2-ol hydrochloride 5.29 g of zinc powder treated with 1N HCl and 0.26 g of lead powder were added to 33.5 ml of tetrahydrofuran and stirred, and 3.98 g of iodine dissolved in 10.6 ml of tetrahydrofuran was slowly added thereto for 10 min while heating to 45° C. The resulting mixture was cooled to 2° C., and a solution dissolving 3.53 g of 1-(2,4-difluorophenyl)-2-(1H-1,2,4-triazol-1-yl)ethanone in 30 ml of tetrahydrofuran, 5 g of 6-(1-bromo-ethyl)-4-chloro-5-fluoropyrimidine and 0.32 g of iodine were slowly added thereto for 10 min. The obtained mixture was heated to 25° C. and reacted for 1 hour.

4.67 g of glacial acetic acid and 12 ml of water were added to the reaction solution, solid metal residue was filtered out, and tetrahydrofuran was removed under a reduced pressure.

The resulting residue was extracted twice with 66 ml of ethyl acetate, and the extract was successively washed with 4.67 g of disodium ethylenediaminetetraacetate dehydrate dissolved in 12 ml of water, and 30 ml of brine. The organic layer was concentrated to 40 ml volume, and 0.86 g of HCl dissolved in 4.3 ml of isopropanol was added thereto at 25° C.

The obtained crystal was filtrated, washed with 10 ml of ethyl acetate, and dried to obtain the title compound as a yellow crystal (2.81 g, yield: 42%).

m.p=126~130° C.

$^1$H-NMR (300 MHz, DMSO-d$_6$) δ (ppm): 8.84 (1H), 8.73 (1H), 7.93 (1H), 7.28 (1H), 7.20 (1H), 6.91 (1H), 4.82 (1H), 4.54 (1H), 3.93 (1H), 1.14 (3H)

The enantiomer ratio obtained from HPLC analysis of the reaction solution by using an internal standard material was 10:1, and 14.39% of unknown byproduct was formed. Further, the ratio of (2R,3S)/(2S,3R)- and (2R,3R)/(2S,3S)-enantiomeric pair obtained from HPLC analysis of the crystallized hydrochloride was 94.4%:4.8%.

While the invention has been described with respect to the above specific embodiments, it should be recognized that various modifications and changes may be made and also fall within the scope of the invention as defined by the claims that follow.

What is claimed is:

1. A process for preparing voriconazole of formula (I), which comprises the steps of:
a) subjecting the compound of formula (IV) to Reformatsky-type coupling reaction with a compound of formula (V) to obtain a compound of formula (III) which is a (2R,3S)/(2S,3R)-enantiomeric pair;
b) removing the thiol derivative from the compound of formula (III) to obtain the racemic voriconazole of formula (II); and
c) isolating the compound of formula (II) by way of optical resolution using an optically active acid:

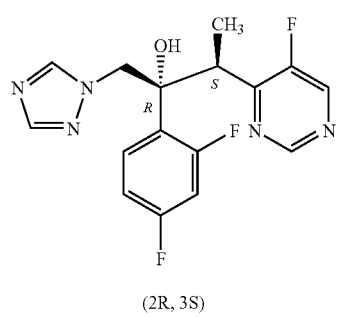

(2R, 3S) (I)

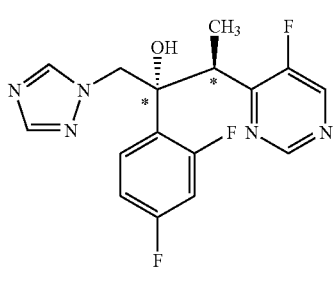

(2R, 3S/2S, 3R) (II)

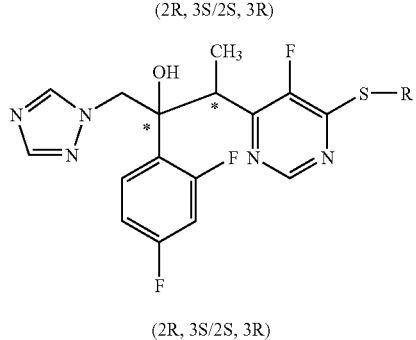

(2R, 3S/2S, 3R) (III)

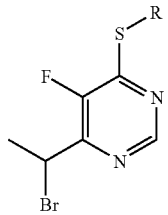

(IV)

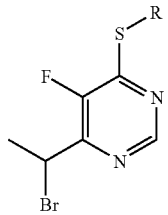

(V)

wherein,
R is $C_1$-$C_4$ alkyl, benzothiazolyl, benzoxazolyl, imidazolyl, 1-methylimidazolyl, thiazolyl, pyridyl, pyrimidyl, phenyl, or phenyl having one or two substituents selected from the group consisting of halogen, nitro and methoxy.

2. The process of claim 1, wherein step b) is carried out by using zinc and ammonium formate.

3. The process of claim 2, wherein the zinc is used in an amount ranging from 3 to 10 equivalents based on the compound of formula (III).

4. A compound of formula (V):

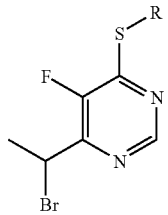

(V)

wherein,
R is $C_1$-$C_4$ alkyl, benzothiazolyl, benzoxazolyl, imidazolyl, 1-methylimidazolyl, thiazolyl, pyridyl, pyrimidyl, phenyl, or phenyl having one or two substituents selected from the group consisting of halogen, nitro and methoxy.

5. The compound of claim 4, which is (i) 4-(1-bromo-ethyl)-6-(4-phenylsulfanyl)-5-fluoropyrimidine or (ii) 4-(1-bromo-ethyl)-6-(4-chloro-phenylsulfanyl)-5-fluoropyrimidine.

6. An enantiomeric compound of formula (III):

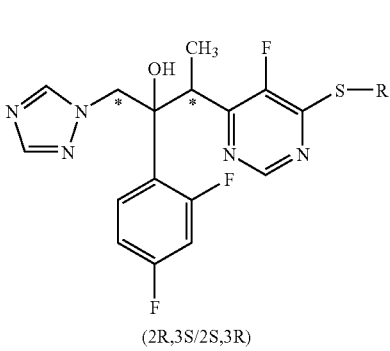

(2R,3S/2S,3R) (III)

wherein,
R is $C_1$-$C_4$ alkyl, benzothiazolyl, benzoxazolyl, imidazolyl, 1-methylimidazolyl, thiazolyl, pyridyl, pyrimidyl, phenyl, or phenyl having one or two substituents selected from the group consisting of halogen, nitro and methoxy.

7. The compound of claim 6, which is (i) (2R,3S)/(2S,3R)-3-[6-(4-phenylsulfanyl)-5-fluoro-pyrimidine-4-yl]-2-(2,4-difluoro-phenyl)-1-[1,2,4]triazol-1-yl-butane-2-ol or (ii) (2R,3S)/(2S,3R)-3-[6-(4-chloro-phenylsulfanyl)-5-fluoro-pyrimidine-4-yl]-2-(2,4-difluoro-phenyl)-1-[1,2,4]triazol-1-yl-butane-2-ol.

* * * * *